US012589027B2

(12) United States Patent
Weyhausen et al.

(10) Patent No.: US 12,589,027 B2
(45) Date of Patent: Mar. 31, 2026

(54) METHOD FOR CENTERING A CONTACT GLASS AND REFRACTIVE SURGICAL LASER SYSTEM

(71) Applicant: Carl Zeiss Meditec AG, Jena (DE)

(72) Inventors: Andreas Weyhausen, Jena (DE); Mark Bischoff, Jena (DE); Gregor Stobrawa, Jena (DE); Marco Lehnort, Jena (DE)

(73) Assignee: Carl Zeiss Meditec AG, jena (DE)

( * ) Notice: Subject to any disclaimer, the term of this patent is extended or adjusted under 35 U.S.C. 154(b) by 383 days.

(21) Appl. No.: 18/248,540

(22) PCT Filed: Oct. 12, 2021

(86) PCT No.: PCT/EP2021/078134
§ 371 (c)(1),
(2) Date: Apr. 11, 2023

(87) PCT Pub. No.: WO2022/078998
PCT Pub. Date: Apr. 21, 2022

(65) Prior Publication Data
US 2023/0372149 A1 Nov. 23, 2023

(30) Foreign Application Priority Data

Oct. 12, 2020 (DE) ..................... 10 2020 212 850.2

(51) Int. Cl.
*A61F 9/00* (2006.01)
*A61F 9/008* (2006.01)

(52) U.S. Cl.
CPC ........ *A61F 9/0061* (2013.01); *A61F 9/00804* (2013.01)

(58) Field of Classification Search
None
See application file for complete search history.

(56) References Cited

U.S. PATENT DOCUMENTS

2002/0036749 A1* 3/2002 Isogai ................... A61B 3/152
351/212
2005/0046794 A1* 3/2005 Silvestrini ........... A61B 3/0091
351/200

(Continued)

FOREIGN PATENT DOCUMENTS

CN 1886690 A 12/2006
CN 108135742 A 6/2018
DE 102009006024 A1 8/2010

OTHER PUBLICATIONS

German search report issued in DE 10 2020 212 850.2 to which this application claims priority of, mailed Jun. 28, 2021.

(Continued)

*Primary Examiner* — Michael T. Holtzclaw

(74) *Attorney, Agent, or Firm* — Pearl Cohen Patentanwälte PartGmbB; Michael McCandlish

(57) ABSTRACT

A method for centering a contact glass relative to a patient's eye includes a) providing a fixation light through a contact glass to align the patient's eye by fixating on the fixation light; b) detecting an image of light pattern that is imaged on the eye's surface; c) presenting the image over the eye with the contact glass with overlaying of virtual markings, wherein a first marking identifies the central axis of the contact glass and a second marking identifies a reference marking, which is derived from the image of the light pattern as lying on the central axis of the contact glass; d) laterally positioning the contact glass such that a distance between the markings is minimized; and e) establishing the position of the eye at which the second marking is located when the markings adopt the minimized distance and registering the position of the vertex.

26 Claims, 5 Drawing Sheets

(56)     References Cited

U.S. PATENT DOCUMENTS

| | | |
|---|---|---|
| 2007/0273828 A1 | 11/2007 | Polland et al. |
| 2008/0071254 A1 | 3/2008 | Lummis et al. |
| 2008/0234707 A1* | 9/2008 | Muehlhoff .............. A61F 9/009 |
| | | 606/166 |
| 2009/0103050 A1 | 4/2009 | Michaels et al. |
| 2009/0163898 A1 | 6/2009 | Gertner et al. |
| 2011/0304819 A1 | 12/2011 | Juhasz et al. |
| 2014/0276678 A1 | 9/2014 | Berry et al. |
| 2015/0018674 A1* | 1/2015 | Scott .................. A61F 9/00827 |
| | | 600/407 |
| 2017/0100282 A1 | 4/2017 | Seiler et al. |

OTHER PUBLICATIONS

International Search Report and Written Opinion issued in PCT/EP2021/078134 to which this application claims priority of, mailed Jan. 24, 2022.

Intention to grant issued in European patent application EP 21 790 462.2, which is a counterpart hereof, dated Aug. 5, 2025, and English-language machine translation thereof.

Office Action by the Chinese Patent Office (SIPO) issued in CN 202180069707.6, which is a counterpart hereof, mailed on Sep. 10, 2025, and English-language machine translation thereof.

Intention to grant issued in European patent application EP 21 790 462.2, which is a counterpart hereof, dated Dec. 23, 2025, and English-language machine translation thereof.

* cited by examiner

METHOD FOR CENTERING A CONTACT GLASS AND REFRACTIVE SURGICAL LASER SYSTEM

CROSS REFERENCE TO RELATED APPLICATIONS

This application is a national stage of international patent application PCT/EP2021/078134, filed on Oct. 12, 2021 and designating the U.S., which claims priority to German patent application DE 10 2020 212 850.2, filed on Oct. 12, 2020, both of which are hereby incorporated by reference in their entireties.

TECHNICAL FIELD

The present disclosure relates to a method for centering a contact glass on a patient's eye, a method for preparing a refractive surgical treatment of an eye, a computing unit, and a refractive surgical laser system. In particular, the disclosure is in the field of laser systems for refractive surgery.

BACKGROUND

Ophthalmological femtosecond lasers are often used for refractive surgical treatments of the eye, with refractive eye corrections being implemented with the laser beam by detaching or removing tissue from the eye, in particular from the cornea. To couple the laser beam into the eye to be treated, a contact glass with a contact surface is typically used, said contact glass being placed on the patient's eye to be treated and being firmly sucked onto the eye in order to fix the eye. The laser beam can then be coupled into the firmly sucked eye through the contact glass and can be applied in a controlled manner to the eye that has been fixed to said contact glass.

In this case, the center of the contact glass, which is typically defined by the vertex of the curved contact glass surface, is used as the geometric origin of all cuts in the eye made by the laser. Therefore, the positioning or centering of the contact glass in relation to the eye determines the location of the cuts in the eye. Precise and controlled positioning and centering of the contact glass is therefore of great importance for the accuracy of the refractive surgical treatment.

The positioning of the contact glass typically comprises the following three phases:

A rough positioning in which the contact glass is located a few centimeters to millimeters above the patient's eye and the contact glass is aligned with the eye.

A fine positioning in which the contact glass is in contact with the eye and is brought into its desired final position relative to the eye.

A suctioned state in which the suction of the eye to the lens, or vice versa, is activated such that the patient's eye is fixed to the contact glass.

Conventional laser systems for refractive surgery provide the physician with various types of assistance within the scope of the rough positioning of the contact glass relative to the patient's eye, for instance a fixation light that allows the eye to angularly align with the contact glass. However, the fine positioning is conventionally carried out by the physician, who defines the exact positioning of the contact glass on the eye, more precisely the desired target point on the cornea, at their own discretion and depending on the type of treatment.

However, the fine positioning is perceived as a challenge as it leads to a high degree of uncertainty in many physicians, and the physician also carries out several or even numerous positioning attempts until a positioning that is satisfactory for the physician is achieved. In this context, a fine positioning or centering of the contact glass is conventionally implemented, for example, in such a way that the physician uses a printed diagnostic image of the eye to be treated, on which the desired positioning point is plotted and on the basis of which the physician tries to orient themselves on the real eye when centering the contact glass. Also, the defined fine positioning conventionally is not logged, with the result that a subsequent analysis in this regard is not possible. A quantitative assessment and logging of the achieved centering (or deviation from the desired target) is therefore only possible manually.

Additionally, within the scope of fine positioning, physicians often intend to move the contact glass or the treatment center again while the eye is sucked on; which is not possible using conventional systems and may therefore require a detachment of the eye from the contact glass and a renewed fixation.

SUMMARY

It is therefore an object of the disclosure to provide methods and a refractive surgical laser system which simplify the fine positioning of the contact glass on the eye for the user or the physician and allow reproducible, reliable fine positioning.

According to the disclosure, this object is achieved by methods, a computing unit, and a refractive surgical laser system as disclosed herein.

In a first aspect, the disclosure relates to a method for centering a contact glass relative to a patient's eye. The method comprises a) a provision of a fixation light by the contact glass such that the patient's eye is aligned relative to the contact glass by fixation on the fixation light. Further, the method comprises b) a capture of an image representation of a light pattern provided by a light source with a fixed spatial relationship relative to the contact glass, with the imaging of the light pattern being implemented via a reflection on the surface of the eye.

Moreover, the method comprises c) a display of the image representation of the light pattern via the eye through the contact glass with overlaid virtual markings, with a first marking of the virtual markings identifying the central axis of the contact glass and a second marking of the virtual markings identifying a reference marking which, from the image representation of the light pattern, is derived as being located on the central axis of the contact glass. Moreover, the method comprises d) a lateral positioning of the contact glass relative to the eye in such a way that a distance between the first and the second marking is minimized; and e) a definition of the location of the eye at which the second marking is situated when the first marking and the second marking are at the minimized distance from one another as the position of the vertex of the eye, and registering the position of the vertex on the basis of a feature of the eye that is recognizable in the image representation of the eye.

In a further aspect, the disclosure relates to a method for preparing a refractive surgical treatment of an eye by means of a laser system. The method for preparing a refractive surgical treatment comprises a method according to the disclosure for centering a contact glass relative to the eye and an ascertainment of an overlap of the pupil of the eye with an optical zone of a lenticule to be extracted during refractive surgical treatment.

In a further aspect, the disclosure relates to a computing unit configured to control a refractive surgical laser system for implementing a method according to the disclosure.

In a further aspect, the disclosure relates to a refractive surgical laser system, typically a femtosecond laser system, with a contact glass. The laser system is configured to a) provide a fixation light by the contact glass in such a way that the patient's eye is aligned relative to the contact glass by fixation on the fixation light.

Furthermore, the laser system is configured to b) capture an image representation of a light pattern provided by a light source with a fixed spatial relationship relative to the contact glass, with the imaging of the light pattern being implemented via a reflection on the surface of the eye.

Moreover, the laser system is configured to c) display an image representation of the light pattern via the reflection on the surface of the eye through the contact glass with overlaid virtual markings, with a first marking of the virtual markings identifying the central axis of the contact glass and a second marking of the virtual markings identifying a reference marking which, from the image representation of the light pattern, is derived as being located on the central axis of the contact glass.

In addition, the laser system is configured to d) laterally position the contact glass relative to the eye in such a way that a distance between the first marking and the second marking is minimized, and e) define the location of the eye at which the second marking is situated when the first marking and the second marking are at the minimized distance as the position of the vertex of the eye, and register the position of the vertex on the basis of a feature of the eye that is recognizable in the image representation of the eye.

In this context, the fixation light being provided by the contact glass means that the contact glass provides the fixation light itself, for example by means of a corresponding light source that has been integrated into the contact glass, or that the fixation light is provided by a separate light source and is transmitted through the contact glass to the eye. Here, the fixation light is a light signal visible to the eye, which is offered to the patient's eye for orientation purposes, so that the eye assumes the desired orientation when the patient's eye is fixated on the fixation light. According to an exemplary embodiment, the light source with the fixed spatial relationship relative to the contact glass can also serve as a fixation light. According to other exemplary embodiments, one or more further light sources can be provided as fixation light.

In this context, "centering the contact glass relative to the eye" means that the contact glass is brought into the desired position in which the refractive surgical treatment is carried out on the eye. Centering in this case does not require the central axis of the contact glass to coincide with the optical axis of the eye. Rather, the contact glass can also be centered on another position of the eye that is desired for the surgical treatment.

In this context, displaying the image representation of the eye and the virtual markings means that these are rendered visible to the user, for example by means of a display unit such as a computer display or another piece of display equipment. In this context, the virtual markings being virtual means that they are optionally only displayed in the representation, for example on the computer display, but are not projected onto the eye or otherwise attached to the eye.

According to other exemplary embodiments, however, the virtual markings can also be projected onto the eye.

In this case, the light source having a fixed spatial relationship to the contact glass means that the position of the contact glass and optionally the position of the central axis of the contact glass can be unambiguously determined from the position of the light source. For this purpose, the light source is optionally arranged directly in and/or on the contact glass. According to an optional embodiment, the light source is at least partially ring shaped and surrounds the contact glass at least partially in the circumferential direction. The light pattern of such a light source can be in the form of a light ring, with the center point of the light ring optionally being located on the central axis of the contact glass.

In this case, the light pattern is a geometric arrangement of light which is recognizable in the image representation. The light pattern is designed so that a distinct point of the light pattern, such as a center and/or a geometric centroid and/or a corner and/or any other unambiguously definable point in the light pattern, can be captured, on the basis of which distinct point the relative position of the central axis of the contact glass can subsequently be determined.

In this case, the light pattern being imaged via a reflection on the surface of the eye means that the beam path of the light is folded at the surface of the eye within the scope of the optical imaging. In this case, the curved surface of the eye optionally acts as an imaging optical element in the manner of a convex mirror.

The disclosure offers the advantage that a physician receives assistance when centering the contact glass, and this enables reliable centering of the contact glass. In particular, the disclosure offers the advantage that reliable centering can be implemented as a standard and can also be carried out by users who do not have many years of experience and expertise.

In addition, the disclosure offers the advantage that a semi-automated or fully automated centering of the contact glass can be implemented by the laser system. This accordingly offers the advantage that the activities to be carried out manually by the user during centration can be reduced, minimized or even completely eliminated.

As a result, the demands in relation to the required knowledge and/or motor skills of the user can be reduced. In addition, the activity and in particular the operation of the laser system can be made easier for the user. Moreover, the risk of errors caused by the user can be reduced.

The disclosure also offers the advantage that the centration of the contact glass can be reliably logged, and in particular the logging can be automated. This increases the reliability and verifiability of refractive surgical treatments.

The fixation light described is typically aligned perpendicular to the optical axis of the treatment optical unit. Optionally, the fixation light can have other angles to the optical axis, which makes it appear to be mobile to the patient. Optionally, the fixation light is able to be switched off. Both allow the physician or user to check whether the patient's eye is actually fixating on the fixation light by virtue of the physician or user switching the fixation light on and off and/or moving the latter and observing the reaction of the eye.

Optionally, the center of the pupil of the eye is used as the feature of the eye that is recognizable in the image representation of the eye. This offers the advantage that it can be reliably ascertained in the image representation of the eye, and the ascertainment moreover can be implemented automatically by means of image evaluation. Optionally, the virtual markings further comprise a virtual marking of the center of the pupil. This offers the advantage that the position of the center of the pupil is also easily recognizable for the user, and the user can use this for orientation purposes on the basis of the virtual marking. Optionally, infrared illumination of the eye can be used to facilitate reliable recognition of the pupil and in particular the center of the pupil even in the case of dark eyes or eyes with a dark-colored iris.

Optionally, the light pattern is a ring light, which is provided by a light source configured as a ring illumination and is directed through the contact glass onto the eye. Alternatively, the ring illumination can also be located outside of the contact glass. The ring is typically arranged concentrically around the central axis of the contact glass. The reflection of the ring illumination on the eye is recognizable in the representation of the image representation of the eye.

The use of the projection ring offers the advantage that the shape of the reflection of the projection ring is changed upon reflection on the curved surface of the eye if the projection ring is not incident perpendicular to and concentrically on the vertex of the eye facing the contact glass. On the basis of the shape deviations of the reflection of the projection ring, it is then optionally possible to draw conclusions about the positioning of the contact glass relative to the eye.

Optionally, the center of the projection ring forms the center of the light pattern. Should the light pattern have additional elements, these are typically arranged concentrically around the center point. This facilitates recognition of the relative positioning of the contact glass relative to the eye on the basis of the deformation of the reflection of the projected marking. Optionally, the light pattern can have a plurality of projection rings, which are optionally arranged concentrically to the central axis of the contact glass. Alternatively or additionally, the light pattern may have a predetermined point pattern.

According to an exemplary embodiment, the light pattern includes a polygon and/or a grid and/or a cross. The polygon can optionally be in the form of a triangle, quadrilateral, hexagon or octagon, with a different number of corners also being possible. In this case, the light pattern is optionally designed in such a way that the reference marking is derivable from a center and/or from a centroid of the light pattern and/or from any other distinct point, which reference marking is derived from the image representation of the light pattern as being located on the central axis of the contact glass.

According to an exemplary embodiment, the light pattern is configured such that the shape of the surface of the eye is at least partially determinable on the basis of distortions in the image representation of the light pattern over the surface of the eye vis-à-vis an image representation of an ideal surface of an eye.

Optionally, the capturing of the image representation of the light pattern via the reflection on the surface of the eye is implemented in such a way that the light pattern and the feature of the eye are recognizable in the image representation. By way of example, this can be achieved by imaging with a sufficiently large depth of field so that both the light source and the surface of the eye and optionally the underlying iris and pupil are sharply imaged in the captured image representation. This offers the advantage that the feature of the eye used to register the position of the vertex is able to be recognized in the same image representation that also depicts the light source or the light pattern. Optionally, imaging is implemented with a depth of field of at least 10 mm, optionally at least 15 mm, optionally at least 20 mm, and optionally at least 30 mm. This offers the advantage that both the plane of the light source and the plane of the feature of the eye can be captured in the depth-of-field range.

Optionally, the contact glass is spaced apart from the eye when steps a) to e) are implemented, with the distance of the contact glass from the eye optionally being in the range from 1 mm to 10 cm. This offers the advantage that the contact glass can be centered when the contact glass is not yet in contact with the eye. This also offers the advantage that the region of the eye that is able to be imaged through the contact glass can be adapted to requirements. Moreover, this offers the advantage that the reflection of the projected marking can, at least in part, be transmitted, detected, and displayed through the contact glass.

Optionally, the method furthermore comprises (f) a reduction in the distance between the contact glass, and the eye and a contacting of the eye with the contact glass, and (g) a fine positioning of the contact glass in the lateral direction relative to the eye such that the central axis of the contact glass is positioned at a predetermined position of the eye, with steps f) and g) optionally being implementable in any order and/or multiple times. This allows fine positioning when the contact glass is already in contact with the eye. This can be particularly advantageous to the effect of this allowing the compensation of changes that result from the contact glass being brought into contact with the eye, for instance deformations of the eye and in particular of the cornea. Fine positioning may also comprise a plurality of iterations in contact with the eye and at a distance from the eye, and thus enables an incremental approach to the desired position and/or a testing of different positions.

Optionally, the method further comprises a determination of a kappa angle on the basis of the position of the vertex and the center of the pupil. This offers the advantage that, in particular, it is possible to recognize particularly large kappa angles, which typically lead to an undesired turning away of the eye when the latter is sucked onto the contact glass. Should a large kappa angle have been ascertained, it is optionally possible to output to the user a message or a warning which indicates the presence of a large kappa angle and the associated risks. A laser system can also optionally be configured to prevent suctioning of the eye if a kappa angle which deviates from a specification by a predetermined amount is ascertained.

Optionally, the virtual markings further comprise a virtual marking of a predetermined point of the eye, the predetermined point of the eye being predetermined by the user. For example, the user can determine one or more points on the eye which are also marked by means of a virtual marking in the representation of the image representation of the eye. For example, the user can provide that point with a virtual marking at which they intend to center the contact glass. In other words, the user can specify one or more (alternative) user-defined positioning targets, which for example can be defined by the physician when planning the treatment, and can optionally also let each of the user-defined positioning target or targets be displayed by means of a virtual marking in the representation of the image representation of the eye.

Optionally, the user can choose to show or hide the virtual markings. For example, the user can to this end provide the coordinates of the point to be marked. The provision of the coordinates of this point can for example be implemented directly (using Cartesian and/or radial coordinates) in relation to the pupil center or the pupil middle (especially in the case of a certain pupil size, to take into account a pupil center shift) or on a topography or a wavefront image or an OCT-generated image (e.g., pachy map, epithelial map) of the eye.

Optionally, step (c) of the method explained above further at least partially comprises a display of a topography and/or wavefront image and/or OCT-generated image of the eye, such as a pachy map and/or an epithelial map). Optionally, the user can choose to show or hide one or more of the aforementioned elements. Optionally, the user can choose a representation of one or more such image information items as a partially transparent overlay and/or switch between the plurality of representations of the image information items.

Optionally, the disclosure further comprises a capture of a reflection of the projected optical marking generated on the eye and a characterization of a shape of the eye on the basis of the captured reflection of the light pattern. This offers the possibility of determining, at least partially in automated fashion, the position of the contact glass relative to the eye by means of image evaluation.

Optionally, steps d) and/or f) and/or g) are implemented by the user, that is to say manually or mainly manually as desired by, and under the guidance of, the user. Alternatively or additionally, the method can be implemented in semi-automated or fully automated fashion.

This offers the advantage that the user's required knowledge can be reduced and, moreover, the work to be performed by the user can be simplified. Both in the case of partially and fully automated implementation, the user can optionally always intervene manually in order to interrupt the automated movements, optionally continue them, or else terminate them and continue them manually. This offers the advantage of allowing a user intervention, for example in the event of a malfunction.

Optionally, the method comprises a check of an overlap of the pupil with the optical zone of the lenticule, optionally including a safety margin. The mesopic pupil is typically used to this end, if necessary also the scotopic pupil. This offers the advantage of being able to reduce the risk of a flawed refractive surgical treatment by virtue of being able to recognize an insufficient overlap already in advance and being able to alert the user in this respect.

Optionally, the method further comprises the implementation of a plausibility check on the determined distance between the position of the vertex and the center of the pupil. Such a plausibility check can be carried out, for example, on the basis of a comparison of the relative position determined according to the method steps described above, and hence also of the distance of the vertex from the center of the pupil, with information that is ascertained separately using other diagnostic equipment, for example by means of a (Scheimpflug) topography device and/or OCT device.

The image representation of the eye through the contact glass can optionally be recorded by means of a digital video camera. The latter can be arranged, for example, on the side of the contact glass distant from the eye and can at least partially capture and detect the light that has been transmitted through the contact glass. According to other exemplary embodiments, an analog video camera can also be used.

Optionally, the refractive surgical laser system and in particular the digital video camera comprises a telecentric optical unit, which eliminates or at least reduces the dependency on the scale of the distance between the contact glass and the eye. This enables a reliable capture of the image representation of the eye by means of the video camera at different distances between the contact glass and the eye.

In this case, the computing unit can optionally be integrated into the laser system or be embodied separately from the laser system. The computing unit can have, for example, a microcontroller and/or a CPU and/or a personal computer, or be designed as such. The computing unit is optionally configured to at least partially control the laser system and optionally to control a digital video camera of the laser system in order to display the captured image representation of the eye on a piece of display equipment and optionally overlay virtual markings. The computing unit can optionally possess further functions.

The features and embodiments specified above and explained below should not only be considered to be disclosed in the respective explicitly mentioned combinations in this case, but are also comprised by the disclosure content in other technically advantageous combinations and embodiments.

BRIEF DESCRIPTION OF THE DRAWINGS

The disclosure will now be described with reference to the drawings wherein.

DESCRIPTION OF EXEMPLARY EMBODIMENTS

Figure 1:
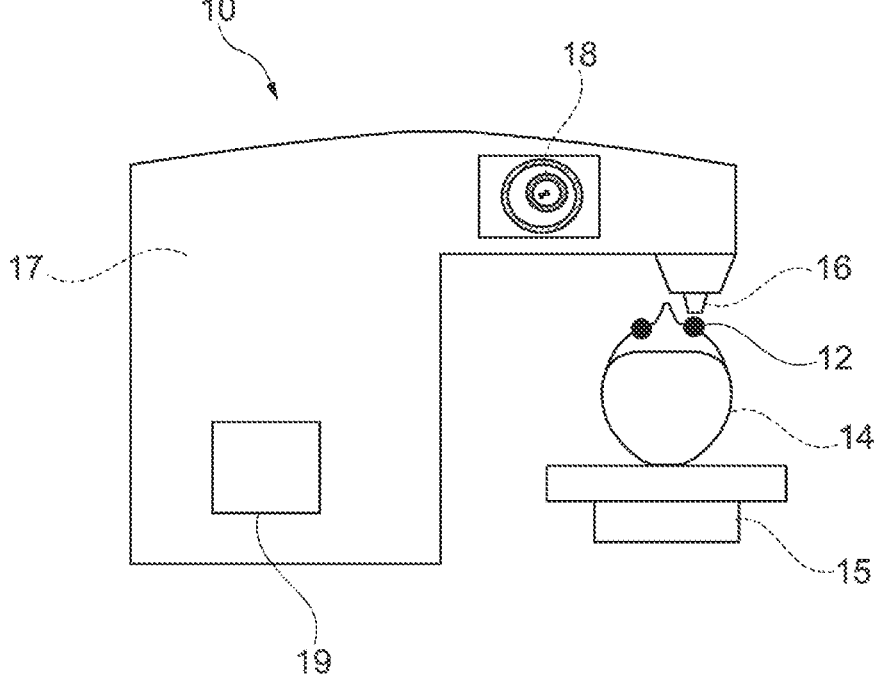
FIG. 1 shows a schematic illustration of a refractive surgical laser system according to an exemplary embodiment.

The same or similar elements in the various exemplary embodiments are denoted by the same reference signs in the drawings for reasons of simplicity.

FIG. 1 shows a schematic illustration of a refractive surgical laser system 10 for carrying out refractive surgical treatments on an eye 12 of a patient 14 in accordance with an exemplary embodiment.

In this case, the laser system 10 comprises a contact glass 16, by means of which the laser system 10 couples to the eye 12 of the patient 14.

To this end, the patient 14 is arranged lying on a couch 15 so that their gaze is directed upward and the laser system 10 can contact and fix the eye vertically from above by means of the contact glass 16.

In addition, the laser system 10 has a femtosecond laser 17 which is integrated into the laser system 10. The laser beam provided by the femtosecond laser 17 is used for the refractive surgical treatment of the eye 12 of the patient 14 and can be applied to the eye 12 through the contact glass 16.

Furthermore, the laser system 10 comprises a display unit 18, by means of which the user of the laser system 10 or the physician can be presented with an image representation of the eye 12 of the patient 14 to be treated and an image representation of a light source 23 arranged on the contact glass 16 via a reflection on the surface of the eye 12. The image representation of the eye 12 to be displayed is brought about through the contact glass 16, for example by means of a digital video camera (not shown) which is integrated into the laser system 10. The image representation of the eye captured by the digital video camera can then be output by the display unit 18 together with overlaid virtual markings so that the physician or user of the laser system 10 can check the eye 12 to be treated and in particular the positioning thereof relative to the contact glass 16.

In this case, the laser system 10 is designed in such a way that a relative movement between the patient 14 and the contact glass and/or laser system 10 can be brought about. To this end, for example, the contact glass can be moved laterally, that is to say perpendicular to the optical axis of the contact glass 16, in order to adopt a suitable positioning of the contact glass for the refractive surgical treatment of the eye 12 and also be moved in the longitudinal direction, that is to say along the optical axis of the contact glass, in order to change the distance between the contact glass 16 and the eye 12 and in particular to fix the contact glass 16 to the eye 12 and detach it from the eye 12. Alternatively or additionally, the patient can be moved vertically using the couch 15.

Moreover, the laser system 10 comprises a computing unit 19 which is configured to control the laser system 10 and display the image representation of the eye 12 on the display unit 18.

Figure 2:
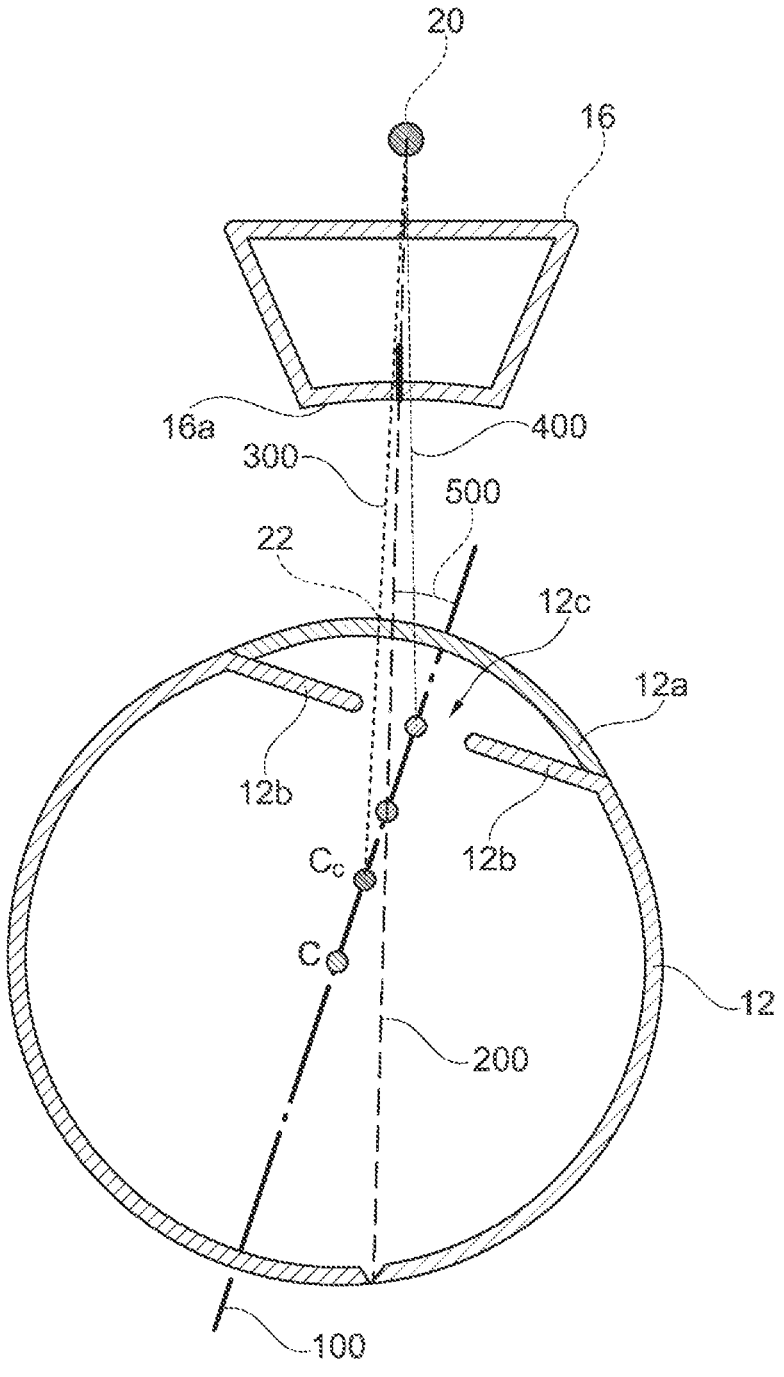
FIG. 2 shows a schematic explanation of the characteristic parameters of the eye and the contact glass.

FIG. 2 explains the geometric parameters of the contact glass 16 and the eye 12 using a schematic representation. In the illustration shown, the contact glass 16 is positioned over the eye 12 and at a distance from the eye 12. On the side facing the eye 12, the contact glass 16 has a curved contact surface 16a, the radius of curvature of which corresponds approximately to the radius of curvature of the cornea 12a of the eye 12. In this case, the contact glass 16 is transparent to the wavelength of the laser beam and optionally also to the visible spectral range, in order to allow the eye to be observed through the contact glass 16. The point light source for a fixation light 20 which propagates through the contact glass toward the eye 12 along a central axis or visual axis 200 of the contact glass 16 is located on the side of the contact glass 16 distant from the eye 12. The terms central axis 200 of the contact glass 16 and visual axis 200 of the contact glass 16 are used synonymously.

In the illustration shown, the eye 12 is positioned and oriented in such a way that the optical axis 100 of the eye 12 runs obliquely to the top right. The optical axis 100 passes through the center C of the eye and centrally through the pupil 12c, which is bounded by the iris 12b.

The center of curvature of the cornea, denoted Cc, is also located on the optical axis 100 of the eye. The connecting line between the position of the point light source of the fixation light 20 and the center of curvature of the cornea Cc represents the keratometric axis 300 here, the corneal vertex 22 being located at the point of intersection of said axis with the outer surface of the cornea 12a.

Further, the line of sight 400 of the eye 12 and the kappa angle 500, that is to say the angle between the optical axis of the eye and the visual axis 200 of the contact glass 16, are plotted for explanatory purposes.

Figure 3:
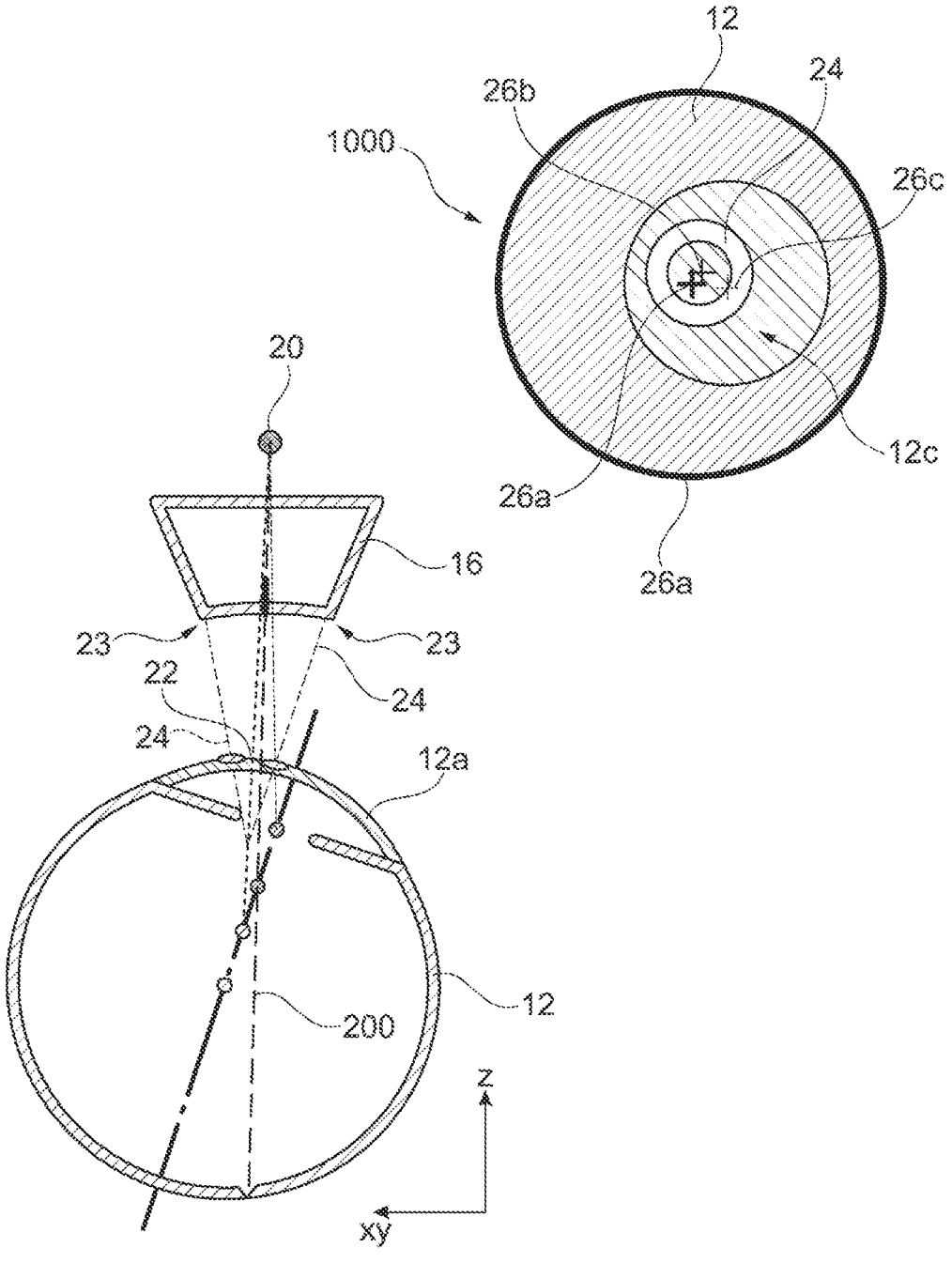
FIG. 3 shows a schematic representation of the relative arrangement of the contact glass in relation to the eye.

A method for centering a contact glass 16 relative to an eye 12 according to an optional embodiment is explained below with reference to FIGS. 3 to 5. In this case, FIGS. 3 to 5 each show a schematic representation of the relative arrangement of the contact glass in relation to the eye 12 in the lower left area and an exemplary representation 1000 of an image representation of the eye 12 with overlaid markings in the upper right area.

In a first step (i), prior to the refractive surgical treatment of the eye 12, the physician ascertains whether the eye 12 has problematic irregularities on the surface which could prevent the treatment. Provided this is not the case, the preparation for the treatment and the centration of the contact glass 16 is continued.

In a second step (ii), the contact glass 16 is fastened to the laser system 10 and the fastened contact glass 16 is positioned over the eye 12 of the patient 14 at a z-distance of several centimeters. The patient is requested to fixate on the fixation light 20 with the eye 12.

In a further step (iii), the laser system 10 uses a light source 23 to project a light pattern 24 onto the eye 12, which light source, according to the exemplary embodiment, is designed as a light ring concentric around the center of the contact glass or around the central axis 200. According to an exemplary embodiment, the light source 23 is arranged in and/or on the contact glass 16 in such a way that the light emitted by the light source 23 emerges along the edge of the contact glass 16 in the direction of the eye 12 and provides the ring-shaped light pattern 24 concentrically in relation to the central axis of the contact glass 16. The light pattern 24 is at least partially reflected by the cornea 12a and is therefore visible in the image representation of the light source 23 and the eye 12 and is shown in the representation 1000 of the image representation of the eye 12. According to the exemplary embodiment shown, the origins of the light rays of the light pattern 24 lie concentrically around the central axis 200 of the contact glass. The light rays reflected on the surface of the eye, by contrast, are arranged concentrically around the keratometric axis.

In the representation 1000 of the image representation of the eye 12, which is recorded through the contact glass 16, the eye 12 and in particular the pupil 12c are recognizable, and also the reflection of the light pattern. Moreover, a plurality of virtual markings 26 is displayed overlaid on the image representation of the eye 12, with the virtual marking 26a identifying the central axis 200 of the contact glass 16 and the edge of the contact glass 16, the virtual marking 26b identifying the reference marking that is derived as located on the central axis of the contact glass from the image representation of the light pattern 24, and the virtual marking 26c identifying the center of the pupil 12c ascertained from the image representation by means of image evaluation.

In a step (iv), the physician can thus recognize the edge of the contact glass, the pupil and the projection ring by way of the representation 1000.

The system determines, optionally in continuous and automated fashion, the center of the pupil, the central axis of the contact glass 16, and the center of the projection ring and displays the corresponding virtual markings 26a, 26b, 26c in a constantly updated position so that the physician can follow them (step (v)).

Figure 4:
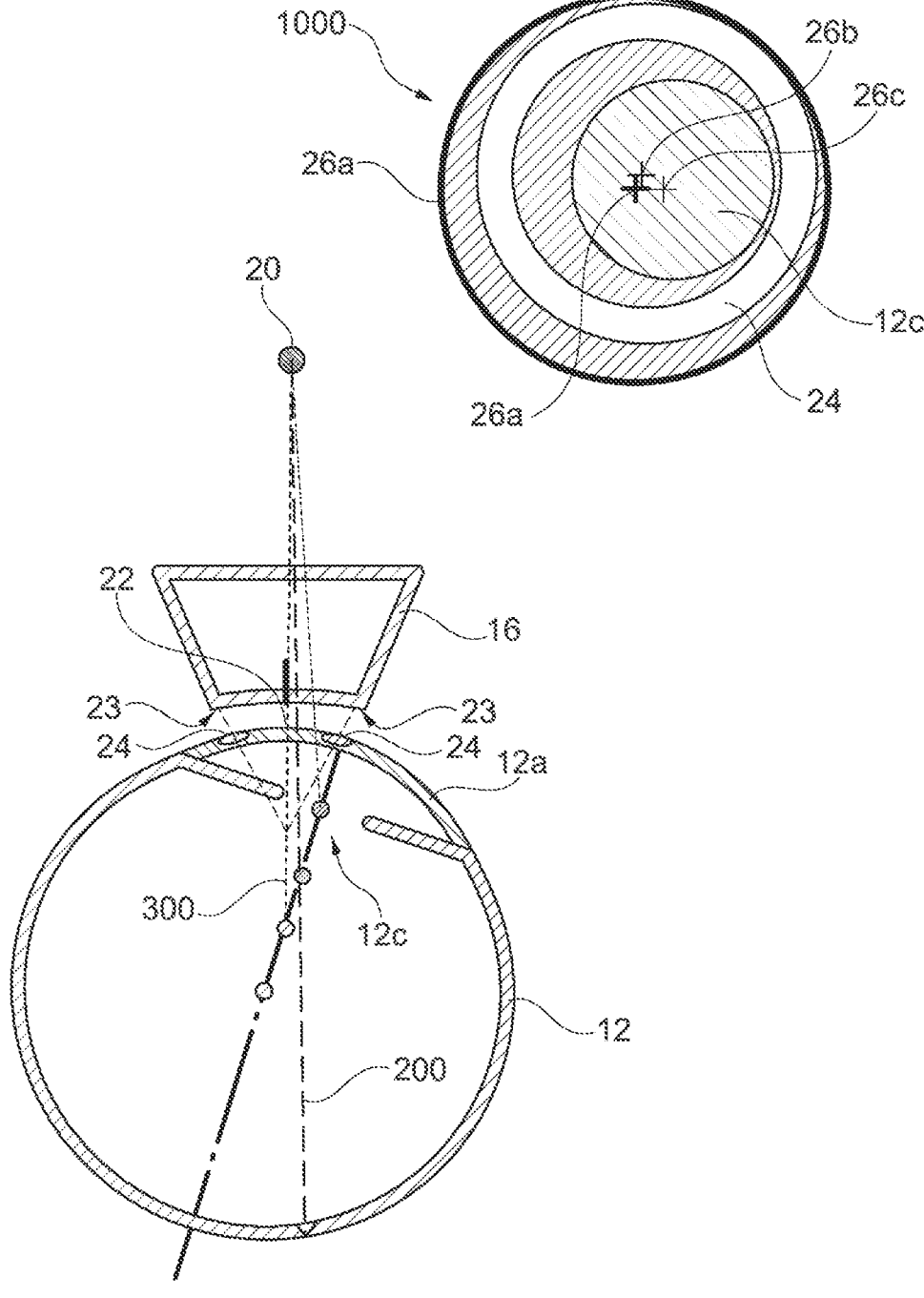
FIG. 4 shows another schematic representation of the relative arrangement of the contact glass in relation to the eye.

In a further step (vi), the physician can then reduce the z-distance between the contact glass 16 and the eye 12, as shown in FIG. 4. The diameter of the projection ring on the eye increases in the process (see representation 1000 in FIG. 4). In the process, the physician reduces the z-distance until the projection ring 24 is larger than the diameter of the pupil 12c but smaller than the diameter of the contact glass 16.

In a further step (vii), the physician pauses the approach of the contact glass 16 to the eye 12 and asks the patient 14 again to fixate on the fixation light 20 with the eye 12. The physician then aligns the center of the contact glass 16 or the central axis 200 of the contact glass 16 with the center point of the light pattern 24 by a lateral displacement of the patient's eye 12 relative to the contact glass 16 (or vice versa). In this case, the center of the light pattern 24 effectively marks the vertex 22 of the eye.

In a further step (viii), the physician causes the system to store the position of the vertex 22 ascertained with the aid of the center of the positioning ring 24. The system defines the ascertained position as the position of the vertex 22 and automatically registers this position on the basis of a feature of the eye 12 that is recognizable in the shown image representation of the eye 12. According to this exemplary embodiment, the laser system 10 uses the center point of the pupil 12*c* as such a feature, since the latter is reliably recognizable and determinable by means of image evaluation. According to other exemplary embodiments, however, other features of the eye 12 can also be used as an alternative or in addition.

The physician subsequently continues to decrease the z-distance between the contact glass 16 and the eye 12 in step (ix). In the process, the position of the vertex stored by the laser system 10 and registered on the basis of the recognizable feature is now continued as a virtual marking 26*b* in the representation 1000 by the laser system 10, even if the projection ring 24 is no longer visible in the image representation on account of the reduced z-distance, as shown in FIG. 5. As a result, the position of the vertex 22 remains recognizable for the physician and can be used for orientation purposes. The physician then centers the central axis 200 of the contact glass 16 on the position of the vertex 22 or on any other point of the eye 12 envisaged to this end.

Figure 5:
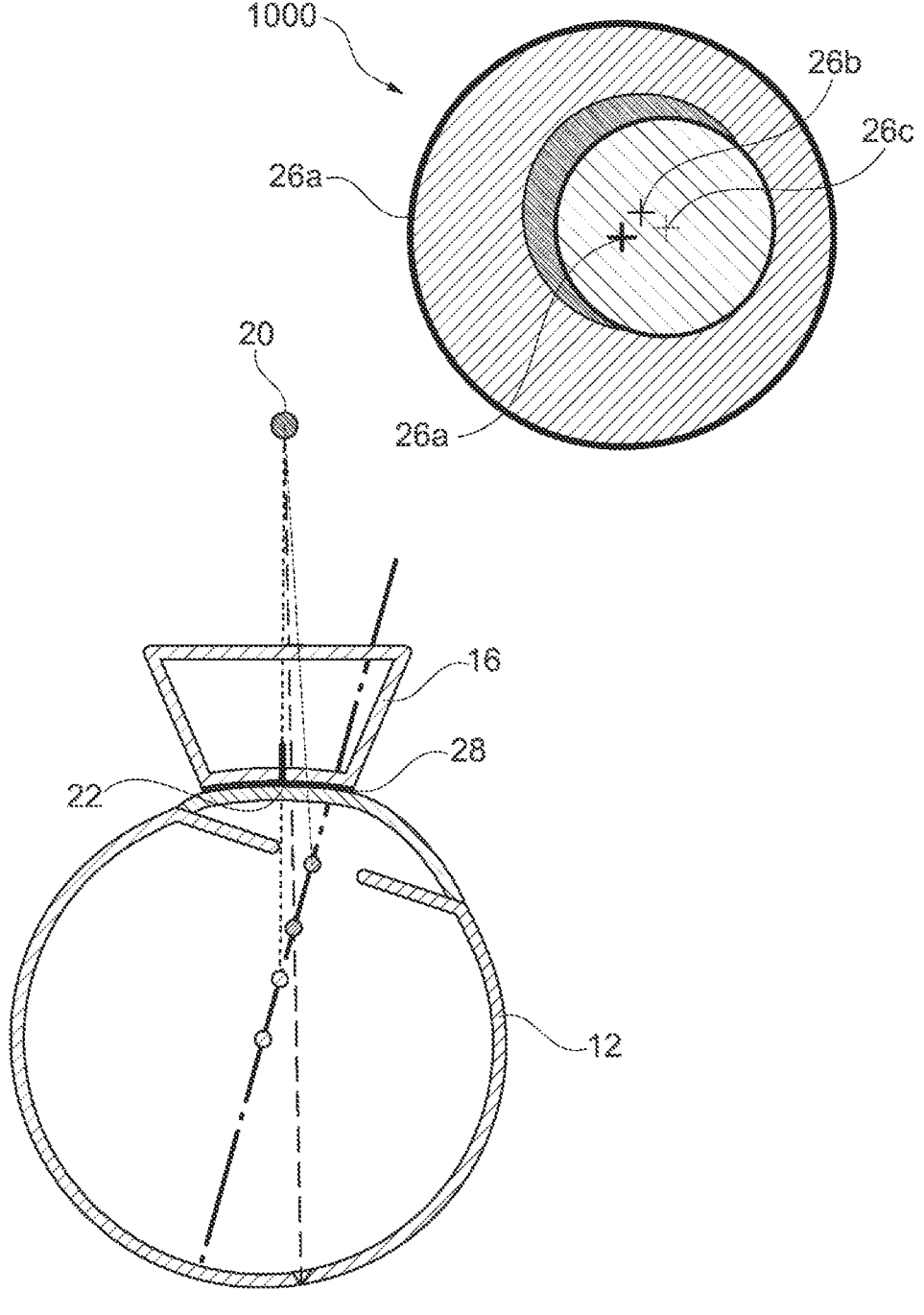
FIG. 5 shows yet another schematic representation of the relative arrangement of the contact glass in relation to the eye.

When the contact glass 16 comes into contact with the eye 12, a water meniscus 28 (tear film) forms between the eye 12 and the contact glass 16, as shown in FIG. 5. The refractive effect of the air between the contact glass 16 and the eye 12 is avoided as a result of the water meniscus. The cornea 12*a* is deformed or applanated as a result of contact with the contact glass 16, with the radius of curvature of the cornea 12*a* adapting to match the radius of curvature of the contact surface 16*a* of the contact glass 16. In this case, the laser system 10 takes into account the deformation of the cornea 12*a* caused by the contact and the change in the imaging scale of the image representation as a result of the water meniscus, and shows the physician the corrected vertex position 22.

Subsequently, in a further step (x), the physician can carry out the fine positioning of the contact glass 16 relative to the eye and, in the process, orient themselves using the virtual markings displayed in the representation.

After the fine positioning is complete, the physician can confirm the completion and cause the eye 12 to be suctioned against and fixed to the contact glass 16.

The laser system 10 then calculates and logs the position of the contact glass 16 relative to the eye 12 and relative to the recognizable feature of the eye, for instance relative to the pupil center, and optionally calculates and logs the diameter of the pupil, and stores this for logging the procedure so that this information is available, if necessary, for a retrospective evaluation of the refractive surgical treatment.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

10 Refractive surgical laser system
12 Eye
12*a* Cornea
12*b* Iris
12*c* Pupil
14 Patient
15 Couch
16 Contact glass
17 Femtosecond laser
18 Display unit for representing an image representation of the eye
19 Computing unit
20 Fixation light
22 Vertex or position of the vertex
23 Light source
24 Light pattern
26 Virtual marking
26*a* Virtual marking of the central axis and the edge of the contact glass
26*b* Virtual marking of the center of the projection ring or the projected optical marking
26*c* Virtual marking of the center of the pupil
28 Water meniscus or tear film
100 Optical axis of the eye
200 Central axis or visual axis of the contact glass
300 Keratometric axis
400 Line of sight of the eye
500 Kappa angle
1000 Representation of the image representation of the eye

The invention claimed is:

1. A method for centering a contact glass relative to an eye of a patient, the method comprising the following steps:
   a) providing a fixation light by the contact glass such that the eye of the patient fixating on the fixation light is aligned relative to the contact glass;
   b) capturing an image representation of a light pattern generated by a light source having a fixed spatial relationship relative to the contact glass, with the capturing the image representation of the light pattern being implemented via a reflection on a surface of the eye;
   c) displaying the image representation of the light pattern reflected via the surface of the eye through the contact glass with overlaid virtual markings, with a first marking of the overlaid virtual markings identifying a central axis of the contact glass and a second marking of the overlaid virtual markings identifying a reference marking which, from the image representation of the light pattern, is derived as being located on the central axis of the contact glass;
   d) laterally positioning the contact glass relative to the eye such that a distance between the first marking and the second marking is minimized;
   e) defining a location of the eye at which the first marking is situated when the first marking and the second marking are at the minimized distance from one another as a position of a vertex of the eye, and registering the position of the vertex based on a feature of the eye that is recognizable in the image representation of the eye.

2. The method as claimed in claim 1, further comprising: illuminating the eye using infrared illumination and recognizing a pupil and optionally a center of the pupil of the eye illuminated by the infrared illumination.

3. The method as claimed in claim 2, wherein the center of the pupil of the eye is used as the feature of the eye that is recognizable in the image representation of the eye and wherein optionally the overlaid virtual markings further include a third marking which identifies the center of the pupil.

4. The method as claimed in claim 1, wherein step c) further comprises at least partially displaying a topography and/or a wavefront image and/or an optical coherence tomography (OCT)-generated image of the eye.

5. The method as claimed in claim 4, further comprising displaying or hiding one or more of the topography and/or the wavefront image and/or the OCT-generated image of the eye, as chosen by a user.

6. The method as claimed in claim 4, further comprising displaying the topography and/or the wavefront image and/or the OCT-generated image of the eye as a partially transparent overlay.

7. The method as claimed in claim 4, wherein the method is implemented in a semi-automated or fully automated manner.

8. The method as claimed in claim 1, further comprising checking an overlap of a pupil with an optical zone of a lenticule to be extracted from the eye.

9. The method as claimed in claim 8, wherein checking the overlap is carried out in consideration of a safety margin.

10. The method as claimed in claim 1, further comprising determining a kappa angle based on the position of the vertex and a center of a pupil.

11. The method as claimed in claim 10, further comprising outputting to a user a message or a warning in case the determined kappa angle deviates from a specification by at least a predetermined amount.

12. The method as claimed in claim 1, wherein displaying the image representation of the light pattern with the overlaid virtual markings is carried out with a display unit.

13. The method as claimed in claim 12, wherein the overlaid virtual markings are only displayed by the display unit without being projected onto the eye.

14. The method as claimed in claim 12, wherein displaying the image representation of the light pattern with the overlaid virtual markings by the display unit further comprises displaying an image of the eye to be treated.

15. The method as claimed in claim 12, wherein the display unit comprises a computer display.

16. The method as claimed in claim 1, wherein the light pattern comprises a ring and/or a polygon and/or a grid, with the reference marking being derivable from a center and/or centroid of the light pattern, the reference marking being derived from the image representation of the light pattern as being located on the central axis of the contact glass.

17. The method as claimed in claim 1, wherein the capturing of the image representation of the light pattern via the reflection on the surface of the eye is implemented such that the light pattern and the feature of the eye are recognizable in the image representation.

18. The method as claimed in claim 17, wherein the capturing of the image representation is implemented with a depth of field of at least 10 mm.

19. The method as claimed in claim 1, wherein the contact glass is spaced apart from the eye when steps a) to e) are implemented and a distance of the contact glass from the eye is in a range from 1 mm to 10 cm.

20. The method as claimed in claim 19, further comprising:

f) reducing the distance between the contact glass and the eye and contacting the eye with the contact glass; and g) finely positioning the contact glass in a lateral direction relative to the eye such that the central axis of the contact glass is positioned at a predetermined position of the eye, with steps f) and g) optionally being implementable in any order and/or multiple times.

21. The method as claimed in claim 1, wherein the overlaid virtual markings further comprise a virtual marking of a predetermined point of the eye, the predetermined point of the eye being predetermined by a user.

22. The method as claimed in claim 1, further comprising capturing the light pattern reflected on the surface of the eye and characterizing a shape of the eye based on the captured reflection of the light pattern.

23. The method as claimed in claim 1, wherein the step d) is implemented by a user.

24. A method for preparing a refractive surgical treatment of an eye with a laser system, the method comprising the method for centering a contact glass relative to the eye as claimed in claim 1; and ascertaining an overlap of a pupil of the eye with an optical zone of a lenticule to be extracted during the refractive surgical treatment.

25. A computing unit configured to control a refractive surgical laser system for implementing a method as claimed in claim 1.

26. A refractive surgical laser system including a femtosecond (fs) laser system with a contact glass, the laser system being configured to:

a) provide a fixation light by the contact glass such that an eye of a patient fixating on the fixation light is aligned relative to the contact glass;

b) capture an image representation of a light pattern generated by a light source having a fixed spatial relationship relative to the contact glass, with the captured image representation of the light pattern being implemented via a reflection on a surface of the eye;

c) display the image representation of the light pattern reflected via the surface of the eye through the contact glass with overlaid virtual markings, with a first marking of the overlaid virtual markings identifying a central axis of the contact glass and a second marking of the overlaid virtual markings identifying a reference marking which, from the image representation of the light pattern, is derived as being located on the central axis of the contact glass;

d) laterally position the contact glass relative to the eye such that a distance between the first marking and the second marking is minimized;

e) define a location of the eye at which the first marking is situated when the first marking and the second marking are at the minimized distance from one another as a position of a vertex of the eye, and register the position of the vertex based on a feature of the eye that is recognizable in the image representation of the eye.

* * * * *